United States Patent
Blair

(10) Patent No.: US 11,690,809 B2
(45) Date of Patent: Jul. 4, 2023

(54) METHOD OF TREATMENT OR ALLEVIATING SYMPTOMS OF A DISORDER WITH CANNABIDIOL

(71) Applicant: Emek Blair, Wellington, CO (US)

(72) Inventor: Emek Blair, Wellington, CO (US)

(73) Assignee: A1C Labs, LLC, Wellington, CO (US)

( * ) Notice: Subject to any disclaimer, the term of this patent is extended or adjusted under 35 U.S.C. 154(b) by 0 days.

(21) Appl. No.: 16/783,430

(22) Filed: Feb. 6, 2020

(65) Prior Publication Data

US 2021/0244682 A1 Aug. 12, 2021

(51) Int. Cl.
| | | |
|---|---|---|
| *A61K 36/185* | (2006.01) | |
| *A61K 31/05* | (2006.01) | |
| *A61K 9/127* | (2006.01) | |
| *A61K 9/00* | (2006.01) | |
| *A61P 3/10* | (2006.01) | |
| *A61K 9/107* | (2006.01) | |

(52) U.S. Cl.
CPC ............ *A61K 31/05* (2013.01); *A61K 9/0053* (2013.01); *A61K 9/1075* (2013.01); *A61K 9/127* (2013.01); *A61K 36/185* (2013.01); *A61P 3/10* (2018.01)

(58) Field of Classification Search
None
See application file for complete search history.

(56) References Cited

PUBLICATIONS

Raskin et al. (2004) Current Pharmaceutical Design, 10: 3419-3429. (Year: 2004).*
Jadoon et al. (2016) Diabetes Care, vol. 39, 1777-1786. (Year: 2016).*
Lehmann et al. (2016) Clinical Hemorhealogy and Microcirculation, 64: 655-662. (Year: 2016).*
Rajesh et al. (2007) Am. J. Physiol. Heart Cirt. Physiol. 293: H610-H619. (Year: 2007).*
Weiss et al. (2006) Autoimmunity 39(2): 143-151. (Year: 2006).*
Frisher et al. (2010) Brit. J. Diabetes & Vasc. Disease, 10: 267-273. (Year: 2010).*
Rajesh et al. (2007) Am. J. Physiol. Heart Circ. Physiol. 293: H610-H619. (Year: 2007).*
Stanley et al. (2013) Eur. J. Pharmacol. 720: 376-382. (Year: 2013).*

\* cited by examiner

*Primary Examiner* — Russell G Fiebig
(74) *Attorney, Agent, or Firm* — Craig R. Miles; CR Miles P.C.

(57) ABSTRACT

A method of treating or alleviating symptoms of a disorder or a condition in a subject, including identifying the disorder or the condition of a subject, the disorder or condition identified based on first measures of a bloodstream concentration of a substance or a blood stream count of cellular elements, orally administering to said subject an amount of cannabidiol over a period of time effective treat or alleviate symptoms of said disorder or said condition, altering the bloodstream concentration of said substance or said blood stream count of cellular elements, and assessing efficacy of treating or alleviating symptoms of the disorder or the condition evidenced by comparing second measures of the bloodstream concentration of the substance or the blood stream count of cellular elements after the period time to the first measures of bloodstream concentration of the substance or the blood stream count of cellular elements.

8 Claims, 1 Drawing Sheet

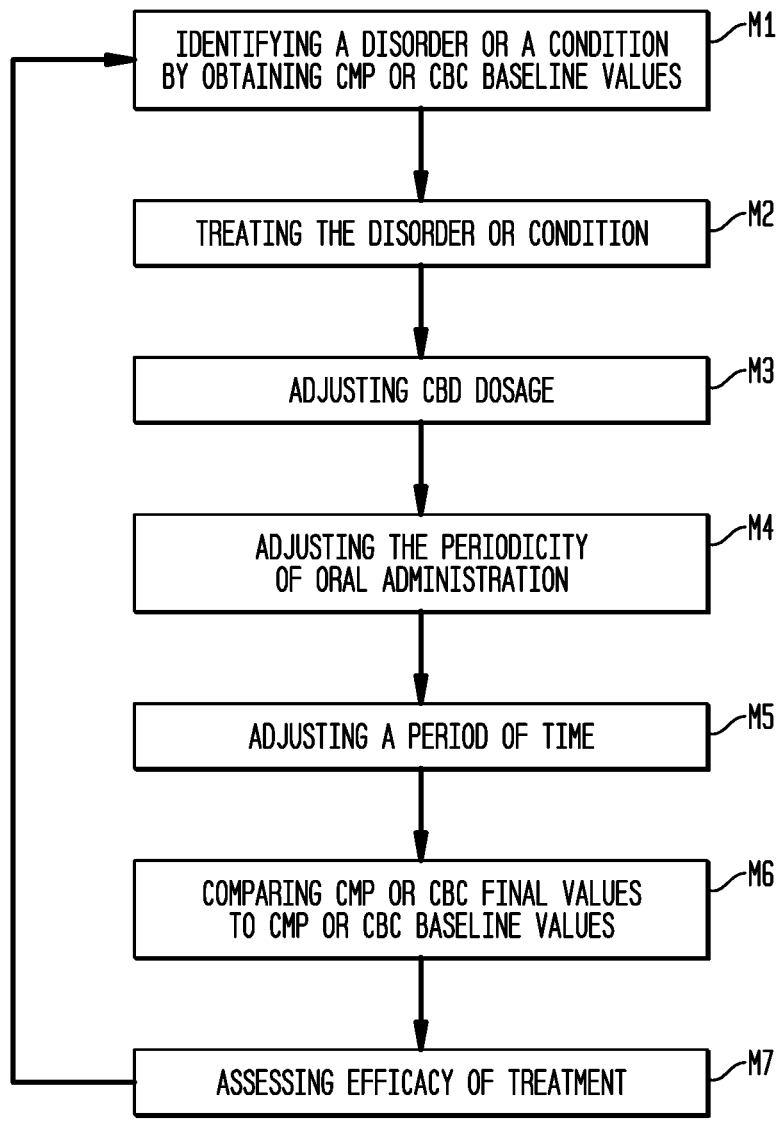

METHOD OF TREATMENT OR ALLEVIATING SYMPTOMS OF A DISORDER WITH CANNABIDIOL

I. FIELD OF THE INVENTION

A method of treating or alleviating symptoms of a disorder or a condition in a subject including orally administering to the subject an amount cannabidiol effective to alter bloodstream concentration of a substance or a blood stream count of cellular elements.

II. BACKGROUND OF THE INVENTION

Although there are numerous mouse and animal studies on cannabidiol ("CBD"), there are limited human studies and no credible randomized controlled human studies assessing efficacy of CBD to treat or alleviate symptoms of a disorder or a condition in a subject by orally administering cannabidiol in an amount effective in the subject to alter bloodstream concentration of a substance or a blood stream count of cellular elements.

There is a long felt but unresolved need to treat or alleviate symptoms of a disorder using CBD including one or more of: a low red blood cell count, a low eosinophil white blood cell count, a low neutrophil white blood cell count, a liver disorder characterized by a blood stream concentration of alanine transaminase of 60 IU/L or higher, prediabetes characterized by a fasting bloodstream concentration of glucose of between 100 mg/dL to 125 mg/dL, and type 2 diabetes characterized by a fasting bloodstream concentration of glucose of 126 mg/dL or higher.

There would be a substantial advantage in a method of treating or alleviating symptoms of a disorder or a condition by altering bloodstream concentration of a substance or by altering a blood stream count of cellular elements by oral administration of CBD, because CBD offers, without a prescription, a non-toxic remedy having no known fatal overdose levels and which is virtually side effect free, outside of the therapeutic benefit.

III. SUMMARY OF THE INVENTION

Accordingly, a broad object of particular embodiments of the invention can be to afford a method of treating or alleviating symptoms of a disorder or a condition in a subject, comprising, consisting essentially of, or consisting of orally administering to a subject CBD in an amount effective in the subject to reduce bloodstream concentration of blood glucose, blood alanine transaminase, or blood bilirubin, or combinations thereof.

Another broad object of particular embodiments of the invention can be to afford a method of treating or alleviating symptoms of a disorder or a condition in a subject, comprising, consisting essentially of, or consisting of orally administering to a subject CBD in an amount effective in the subject to increase one or more of red blood cell count, eosinophil white blood cell count and neutrophil white blood cell count, or combinations thereof.

Another broad object of particular embodiments of the invention can be to afford a method of altering or adjusting within a normative value range one more of bloodstream concentration of blood glucose, blood alanine transaminase, blood bilirubin, or one or more of red blood cell count, eosinophil white blood cell count and neutrophil white blood cell count.

Naturally, further objects of the invention are disclosed throughout other areas of the specification, drawings, photographs, and claims.

IV. BRIEF DESCRIPTION OF THE DRAWINGS

FIG. 1 is a block flow diagram of a method of treating or alleviating a disorder or condition in a subject.

V. DETAILED DESCRIPTION OF THE INVENTION

Generally, a method of treating or alleviating symptoms of a disorder or disease, or of altering normative values of a condition in a subject comprising, consisting essentially of, or consisting of orally administering to a subject cannabidiol in an amount effective in the subject to alter bloodstream concentration of a substance or a blood stream count of cellular elements. Specifically, a method of treating or alleviating symptoms of a disorder or disease, or of altering normative values of a condition in a subject comprising, consisting essentially of, or consisting of orally administering to a subject cannabidiol in an amount effective in the subject to reduce bloodstream concentration of one or more of: blood glucose, blood alanine transaminase, or blood bilirubin, or effective in a subject to increase one or more of red blood cell count, eosinophil white blood cell count and neutrophil white blood cell count, or combinations thereof.

"A" or "an" entity means one or more of that entity; for example, "a polymer" refers to one or more polymers or at least one polymer. As such, the terms "a" or "an", "one or more" and "at least one" can be used interchangeably herein. Furthermore, the language "selected from the group consisting of" refers to one or more of the elements in the list that follows, including combinations of two or more of the elements.

"About" means that ranges may be expressed as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. In the context of such a numerical value or range "about" means plus or minus 10% of the numerical value or range recited or claimed unless otherwise specified, or the values within the range are incrementally divided into lesser percentage between ranges or values.

"Bloodstream Concentration" for purposes of this invention means an amount of a particular substance in a specific amount of blood, and without sacrificing the breadth of the foregoing, can be expressed as kilograms/meter3 (milligrams per deciliter (mg/dL)) or equivalent measure.

"Cannabidiol (CBD)" for the purposes of this invention means a phytocannabinoid having the formula $C_{21}H_{30}O_2$ having molar mass of 314.464 g/mol and a density of 920 kg/m$^3$ and a CAS ID 13956-29-1. CBD can be obtained as an extract which fulfils the definition of a "botanical drug substance" provided in the *Guidance for Industry Botanical Drug Products*, June 2004, US Department of Health and Human Services, Food and Drug Administration Centre for Drug Evaluation and Research of: "A drug substance derived from one or more plants, algae, or macroscopic fungi,", or combinations thereof. In particular embodiments, CBD can, but need not necessarily, be extracted from a botanical biomass, such as, the stalks, stems and flowers of the *Cannabis sativa* plant. The cannabidiol extracted from a botanical biomass can be a component of a full-spectrum CBD extract which includes all of the cannabinoids extracted from the botanical biomass, or can, but need not necessarily be, a CBD extract which includes only a portion of all of the cannabinoids extracted from the botanical biomass. A CBD extract of a botanical biomass can include CBD by weight occurring in a range of about 20% to about 80%. CBD can, but need not necessarily be, a CBD isolate separated from the full spectrum CBD, which CBC isolate can have a purity in the range of up to about 99% by weight. In particular embodiments, the CBD extract or mixture of CBD extracts of a botanical biomass, or the CBD isolate or a mixture of CBD isolates separated from a CBD extract or mixture of extracts, or synthetic CBD, or combinations thereof can have a weight percent occurring in the range of about 90% to about 99%, or can be selected from the group consisting essentially of or consisting of: about 91% to about 93%, about 92% to about 94%, about 93% to about 95%, about 94% to about 96%, about 95% to about 97%, and about 96% to about 98%. In particular embodiments the CBD extract or CBD isolate can, but need not necessarily, contain an amount of tetrahydrocannabinol ("THC") CAS ID 1972-08-3; however, in particular embodiments the CBD extract, isolate or mixture can, but need not necessarily, contain a weight percent THC in a range of essentially zero to about 0.5%, and in particular embodiments, can contain a weight percent THC of less than 0.05%. In particular embodiments, the weight percent THC can be selected from the range of about 0.01% to about 0.1%, or a weight percent THC selected from the group consisting essentially of or consisting of: about 0.02% to about 0.04%, about 0.03% to about 0.05%, about 0.04% to about 0.06%, about 0.05% to about 0.07%, about 0.06% to about 0.08%, about 0.07% to about 0.09%. In particular embodiments, the CBD can, but need not necessarily, be chemically synthesized and used alone or in combination with CBD extracts or CBD isolates obtained from a botanical biomass.

"CELLg8™" is a trademark associated with a liposomal CBD product available from Pulpo LLC, 126 Raquette Dr. #1, Fort Collins, Colo. which contains CBD which may be derived from hemp in a concentration of 10 mg/mL, lipids which may be derived from sunflowers, tetrahydrocannabinol <0.5%, water <1 microS/cm, and a taste mask.

"Combination or combining" for the purposes of this invention means any method of putting two or more materials together. Such methods include, but are not limited to, mixing, blending, commingling, concocting, dispersing, homogenizing, incorporating, intermingling, fusing, joining, shuffling, stirring, coalescing, integrating, confounding, joining, uniting, or the like.

"Complex" for the purposes of this invention means a molecular entity formed by chemical association involving two or more component molecular entities.

"Condition" for the purposes of this invention means the measurable state of a subject whether within normative values for a particular measured state.

"Complete Blood Count (CBC)" for the purposes of this invention means a count of cellular elements of blood to provide measured values including at least one of red blood cell count, eosinophil white blood cell count, or neutrophil white blood cell count.

"Comprehensive Metabolic Panel (CMP)" for the purposes of this invention means chemical screen (CPT code 80053) of 16 blood tests which provides measured values of substances in the blood including at least one of blood glucose, blood alanine transaminase, or blood bilirubin.

"Disorder" for the purposes of this invention means a disease or ailment of a subject characterized by measurable values outside of the normative values for the subject, and without limitation to the breadth of the foregoing, includes one or more of prediabetes, diabetes, a liver disorder characterized by high blood stream concentration of alanine transaminase, a liver disorder characterized by high blood stream concentration of bilirubin, low red blood cell count, low eosinophil white blood cell count, low neutrophil white blood cell count, or bloodstream concentration of one or more of blood glucose, blood alanine transaminase, or blood bilirubin outside the normative values for the subject.

"Effective" for the purposes of this invention means effecting change in a measurable value.

"Equivalent" for the purposes of this invention means a drug or chemical containing similar amounts of the same ingredients as another drug or chemical or having similar chemical structures, properties or functions to another drug or chemical.

"Hemp" for the purposes of this invention means *Cannabis sativa*, also referred to as industrial hemp, plant of the family Cannabaceae.

"Lipid" for the purposes of this invention means a substance insoluble in water and soluble in alcohol, ether, and chloroform and without limitation to the breadth of the foregoing include fatty acids, neutral fats, waxes and steroids (like cortisone), compound lipids (lipids complexed with another type of chemical compound) including, but not necessarily limited to, lipoproteins, glycolipids and phospholipids which may, but need not necessarily, be derived from botanical biomass such as sunflower seed, rapeseed, egg, soy, algae, or animal biomass such as fish, or combinations thereof.

"Liposome" for the purposes of this invention means an aggregate of molecules comprising at least one lipid bilayer having the nonpolar region of the molecules of the bilayer sequestered between the polar or charged groups of the molecules which afford an inner shell surrounding an aqueous solution core and outer shell in contact with an aqueous solution. Hydrophilic substances dissolved in the core do not readily pass through the bilayer. Hydrophobic substances associate with the bilayer. A liposome or plurality of liposomes, whether separate or in aggregate, can be loaded with hydrophobic or hydrophilic molecules, or a combination thereof, or form a complex with hydrophobic or hydrophilic molecules, or be combined with hydrophobic or hydrophilic molecules. To deliver the molecules to a site of action, the lipid bilayer can fuse with other bilayers such as cell membranes, allowing delivery of the liposome contents, or complexed or combined molecules.

"Liposomal CBD" for the purposes of this invention means a liposome containing, complexed with or combined with an amount of CBD, and without sacrificing the breadth of the forgoing can be CBD contained in the aqueous core or lipid bilayer of a liposome, CBD as a complexed with a liposome, or CBD combined with liposome even if not contained in or complexed with a liposome, or combinations thereof in a composition.

"Micelle" for the purposes of this invention means an aggregate of molecules having both polar or charged groups or molecules and nonpolar regions or molecules, where the polar or ionic groups or molecules form an outer shell in contact with a solution, and the nonpolar region or molecules are sequestered on the interior of the shell. A micelle can contain, be complexed with, or combined with hydrophobic or hydrophilic molecules. To deliver the molecules to a site of action, the micelle can fuse with other bilayers such as cell membranes, allowing delivery of the micelle contents, or complexed or combined molecules.

"Micellular CBD" for the purposes of this invention means a micelle containing, complexed with or combined with an amount of CBD, and without sacrificing the breadth of the forgoing can be CBD contained in a micelle, CBD as a complexed with a micelle, or CBD combined with liposome even if not contained in or complexed with a liposome, or combinations thereof in a composition.

"Normative Values" for the purposes of this invention means the norm or the standard value for a particular measured parameter and without limitation to the breadth of the foregoing means a normal range of concentration for a particular particle or substance in the blood.

"Oral" or "Orally" for the purposes of this invention means delivered through the cavity of the mouth.

"Taste Mask" for the purposes of this invention means an agent(s) useful to mask the taste of an orally administered drug, medicament, substance, or CBD and without limitation to the foregoing, such as anethole, dihydroanethole, eugenol, wintergreen, vanillin, ethylvanillin, ethyl maltol, or the like.

"Subject" for the purposes of this invention means a human evaluated for or undergoing a method of treatment in accordance with an embodiment of the invention.

"Symptom" for the purposes of this invention means a physical or mental feature regarded as indicating a condition of a disease or a condition.

"Treating" or "Treatment" for the purposes of this invention means management and care of a subject by oral administration of CBD in an amount effective to act on or alter a disease or disorder or condition of the subject or alleviate symptoms thereof.

Now, with primary reference to FIG. 1, the method can include identifying a disorder or a condition of a subject by performing first blood tests of a subject to establish CMP or CBC baseline values (Block M1).

The method can further include treating the disorder or condition or alleviating symptoms of the disorder or condition by orally administering to the subject an amount of CBD over a period of time (Block M2). In particular embodiments the amount of CBD can comprise, consist essentially of, or consist of a CBD dosage in the range of a range of 2 milligrams to about 100 milligrams. In particular embodiments, the CBD dosage can be selected from the group consisting of: about 3 milligrams to about 5 milligrams, about 4 milligrams to about 6 milligrams, about 5 milligrams to about 7 milligrams, about 6 milligrams to about 8 milligrams, about 7 milligrams to about 9 milligrams, about 8 milligrams to about 10 milligrams, about 9 milligrams to about 11 milligrams, about 10 milligrams to about 12 milligrams, about 11 milligrams to about 13 milligrams, about 12 milligrams to about 14 milligrams, about 13 milligrams to about 15 milligrams, about 14 milligrams to about 16 milligrams, about 15 milligrams to about 17 milligrams, about 16 milligrams to about 18 milligrams, about 17 milligrams to about 19 milligrams, about 19 milligrams to about 21 milligrams, about 20 milligrams to about 22 milligrams, about 21 milligrams to about 23 milligrams, about 22 milligrams to about 25 milligrams, about 24 milligrams to about 26 milligrams, about 25 milligrams to about 27 milligrams, about 26 milligrams to about 28 milligrams, about 27 milligrams to about 29 milligrams, about 28 milligrams to about 30 milligrams, about 29 milligrams to about 31 milligrams, about 30 milligrams to about 32 milligrams, about 31 milligrams to about 33 milligrams, about 32 milligrams to about 34 milligrams, about 33 milligrams to about 35 milligrams, about 34 milligrams to about 36 milligrams, about 35 milligrams to about 37 milligrams, about 36 milligrams to about 38 milligrams, about 37 milligrams to about 39 milligrams, about 38 milligrams to about 40 milligrams, about 39 milligrams to about 41 milligrams, about 40 milligrams to about 42 milligrams, about 41 milligrams to about 43 milligrams, about 42 milligrams to about 44 milligrams, about 43 milligrams to about 45 milligrams, about 44 milligrams to about 46 milligrams, about 45 milligrams to about 47 milligrams, about 46 milligrams to about 48 milligrams, about 47 milligrams to about 49 milligrams, about 48 milligrams to about 50 milligrams, about 49 milligrams to about 51 milligrams, about 50 milligrams to about 52 milligrams, about 51 milligrams to about 53 milligrams, about 52 milligrams to about 54 milligrams, about 53 milligrams to about 55 milligrams, about 54 milligrams to about 56 milligrams, about 55 milligrams to about 57 milligrams, about 56 milligrams to about 58 milligrams, about 57 milligrams to about 59 milligrams, about 58 milligrams to about 60 milligrams, about 59 milligrams to about 61 milligrams, about 60 milligrams to about 62 milligrams, about 61 milligrams to about 63 milligrams, about 62 milligrams to about 64 milligrams, about 63 milligrams to about 65 milligrams, about 64 milligrams to about 66 milligrams, about 65 milligrams to about 67 milligrams, about 66 milligrams to about 68 milligrams, about 67 milligrams to about 69 milligrams, about 68 milligrams to about 70 milligrams, about 69 milligrams to about 71 milligrams, about 70 milligrams to about 72 milligrams, about 71 milligrams to about 73 milligrams, about 72 milligrams to about 74 milligrams, about 73 milligrams to about 75 milligrams, about 74 milligrams to about 76 milligrams, about 75 milligrams to about 77 milligrams, about 76 milligrams to about 78 milligrams, about 77 milligrams to about 79 milligrams, about 78 milligrams to about 80 milligrams, about 79 milligrams to about 81 milligrams, about 80 milligrams to about 82 milligrams, about 81 milligrams to about 83 milligrams, about 82 milligrams to about 84 milligrams, about 83 milligrams to about 85 milligrams, about 84 milligrams to about 86 milligrams, about 85 milligrams to about 87 milligrams, about 86 milligrams to about 88 milligrams, about 87 milligrams to about 89 milligrams, about 88 milligrams to about 90 milligrams, about 91 milligrams to about 93 milligrams, about 92 milligrams to about 94 milligrams, about 93 milligrams to about 95 milligrams, about 94 milligrams to about 96 milligrams, about 95 milligrams to about 97 milligrams, about 96 milligrams to about 98 milligrams, and about 97 milligrams to about 99 milligrams.

In particular embodiments, the method can further include adjusting the CBD dosage based on the form in which the CBD is orally administered whether as a full spectrum CBD extract obtained from hemp, a CBD isolate, micellular CBD, liposomal CBD, CBD suspension, CBD dispersion, CELLg8™, or combinations or equivalents thereof (Block M3). As an illustrative example, oral administration of liposomal CBD or CELLg8™ can provide the substantial advantage of a reduced CBD dosage. In particular embodiments, the CBD dosage can comprise, consist essentially of, or consist of liposomal CBD or CELLg8™ in the range of about 2 mg to about 15 milligrams of CBD, and in particular embodiments the CBD dosage can be within a range of about 8 mg to about 12 milligrams, and in particular embodiments the CBD dosage can be about 10 mg. This advantageous delivery system can be compared to full spectrum CBD extract, CBD isolate or other forms exclusive of liposomal CBD or CELLg8™ which may require substantially greater CBD dosage to afford the equivalent efficacy.

In particular embodiments, the method can further include adjusting the periodicity of oral administration of the CBD dosage (Block M4). The periodicity of oral administration can vary based on the administered dosage form and CBD dosage. In particular embodiments, the periodicity of oral administration can occur within the range of three times daily to once every seven days. In particular embodiments, the periodicity of oral administration can be selected from the group including, consisting essentially of, or consisting of: twice daily, once daily, once every two days, once every three days, once every four days, once every five days, once every six days. As one illustrative example, oral administration of liposomal CBD or CELLg8™ containing a CBD dosage in the range of 5 mg to 15 mg of CBD, can be orally administered once daily to achieve efficacious results over a period of time.

In particular embodiments, the method can include adjusting a period of time over which periodic oral administration of the CBD dosage occurs (Block M5). The period of time can be coordinated with the dosage form and CBD dosage. In particular embodiments, oral administration of a CBD dosage at a particular periodicity of administration can be maintained indefinitely in the absence of any adverse events or side effects. In particular embodiments, the method can include a period of time between obtaining CMP or CBC baseline values and establishing one or more CMP or CBC final values after periodically orally administering a particular CBD dosage form and a particular CBD dosage for a period of time within the range of consecutive 15 days to 60 days. Depending on the CBD dosage form, the CBD dosage and the periodicity of oral administration, the period of time can be selected from the group including, consisting essentially of or consisting of: about 16 days to about 25 days, about 20 days to about 30 days, about 25 days to about 35 days, about 30 days to about 40 days, about 35 days to about 45 days, about 40 days to about 50 days, about 45 days to about 55 days, and about 50 days to about 59 days. As one illustrative example, in determining efficacy of once daily oral administration of liposomal CBD or CELLg8™ at a CBD dosage of 10 mg, second blood tests of the subject to establish CMP or CBC final values can be performed after elapse of a period time of about 30 days.

The method can further include comparing one or more CMP or CBC final values to corresponding CMP or CBC baseline values (Block M6). As one illustrative example shown by Table 1 and by Table 2, the CMP or CBC final values can be compared to corresponding CMP or CBC baseline values related to the disorder or condition. In the illustrative example of Table 1 the CMP baseline values can be compared to CMP final values and CMP normative values for each of blood glucose, blood alanine transaminase, blood bilirubin, creatinine, or carbon dioxide, or combinations thereof; however, this illustrative example is not intended to preclude embodiments which include a comparison of a lesser or greater number of CMP baseline values, CMP final values, or CMP normative values. In the illustrative example of Table 2, the CMP baseline values can be compared to CMP final values and CMP normative values for each of blood glucose, blood alanine transaminase, blood bilirubin, creatinine, or carbon dioxide, or combinations thereof; however, this illustrative example is not intended to preclude embodiments which include a comparison of a lesser or greater number of CMP baseline values, CMP final values, or CMP normative values.

The method can further include assessing efficacy of treating the subject by based upon evidence of movement from CMP or CBC baseline values identified as the disorder or condition or symptom toward or to CMP or CBC final values within the CMP or CBC normative value or range (Block M7). With reference to Table 1, as one illustrative example, the CMP baseline value for blood glucose can be compared to CMP final value for blood glucose and the CMP normative range values for blood glucose. As evidenced by Table 1, in particular subjects (Participants 3, 4, 5, 7, and 8), the CMP final values move closer to or within the CMP normative range values for blood glucose evidencing efficacy of the inventive method of treatment. With reference to Table 2, as one illustrative example, the CBC baseline value for red blood cell count can be compared to CBC final value for red blood cell count, and the CBC normative range values for red blood cell count. As evidenced by Table 2, in particular subject (Participant 1) the CBC final value for red blood cell count moves closer to or within the CBC normative range values for red blood cell count evidencing efficacy of the method of treatment; however, this illustrative example is not intended to preclude embodiments which include a comparison of a lesser or greater number of CBC baseline values, CB final values, or CBC normative values.

The method can further include adjusting the amount of CBD orally administered to the subject over a second or more periods of time based on assessing efficacy of prior treating the subject. Adjusting the amount of CBD can comprise one or more of changing the CBD dosage form, changing the CBD dosage, or changing the periodicity of oral administration of the CBD dosage. As one illustrative example, the CBD dosage form and the periodicity of oral administration of the CBD dosage may remain the same as in the prior treatment, and the CBD dosage can be increased within the range of about 2 mg to about 100 mg.

The method can further include repeating blood tests to obtain repeated CMP and CBC initial and final values to allow corresponding repeated comparison of CMP and CBC initial and final values to assess efficacy of the treatment of a subject using one or more embodiments of the inventive method.

EXAMPLE I

Subjects. Subjects included ten individuals each between 25 to 70 years of age of generally good health and not ingesting CBD at CMP or CBC baseline who were recruited from the general population in Colorado. Exclusion criteria for subjects included the inability to complete the treatment protocol or the presence of a terminal illness. Subjects after fasting for eight hours, completed a blood draw for establishing CMP and a CBC baseline values.

Disorder or Condition. The CMP and CBC baseline values evidenced that seven out of ten of the subjects had at least one CMP or CBC baseline value that was above or below the normative values in the applicable CMP or CBC reference range.

Treatment. Subjects were each orally administered 10 mg of liposomal CBD once daily for a consecutive thirty-day period without any lifestyle changes. Subjects completed a final blood draw and CMP and CBC final values were compared to CMP and CBC baseline values.

Results. Of 340 blood tests that were performed on the CMP and CBC combined, 339 remained relatively the same or improved after thirty days of once daily oral administration of 10 mg of liposomal CBD. Additionally, seven of the ten subjects having at least one CMP or CBC baseline value that was above or below the CMP or CBC reference range evidenced CMP or CBC final values that were within normative values after thirty days of once daily oral administration of 10 mg of liposomal CBD. Two subjects had a CMP or CBC final value that changed from normal to high at day thirty.

Table 1. Now, with reference to Table 1—CMP Measures, seven of ten of the CMP baseline values that were above or below the CMP normative range normalized after once daily oral administration of 10 mg of liposomal CBD for thirty days.

Fasting Glucose. In regard to CMP fasting glucose values, it was observed in all five subjects that exhibited CMP baseline values above normative glucose values (Participants 3, 4, 5, 7, and 8) that the CMP final value evidenced a return to normative CMP values after once daily oral administration of 10 mg of liposomal CBD for thirty days.

Alanine Transaminase. In regard to CMP alanine transaminase values, one subject (Participant 3) exhibited a CMP baseline value for alanine transaminase outside of the CMP normative range and that the CMP final value evidenced a return to the normative CMP values after once daily oral administration of 10 mg of liposomal CBD for thirty days.

Bilirubin. In regard to CMP bilirubin values, one subject (Participant 10) exhibited CMP baseline values for bilirubin outside of the CMP normative value range and that the CMP final value evidenced a return to the normative CMP value after once daily oral administration of 10 mg of liposomal CBD for thirty days.

Table 2. Now with reference to Table 2—CBC Measures, 5 subjects (Participants 1, 2, 4, 6 and 9) exhibited CBC baseline values outside of CBC normative values.

Red Blood Cell Count. The CBC red blood cell count for one subject (Participant 1) exhibited CBC baseline value for red blood cell count outside the CBC normative value and that the CBC final value evidenced a return to the CBC normative value after once daily oral administration of 10 mg of liposomal CBD for thirty days.

Hematocrit. The CBC hematocrit value for one subject (Participant 1) exhibited a CBC baseline value for hematocrit outside the CBC normative value and that the CBC final value evidenced a return to CBD normative values after once daily oral administration of 10 mg of liposomal CBD for thirty days.

No Side Deleterious Side Effects. CMP and CBC values that were outside of the normative range at CMP or CBC baseline which did not return to the CMP or CBC normative range did not worsen. Results demonstrate that no deleterious effects of liposomal CBD on CMP or CBC values were found in any of the ten subjects (Participants 1-10) after once daily oral administration of 10 mg of liposomal CBD for thirty days. Additionally, ten CMP or CBC values outside of the CMP or CBC normative range at baseline were normalized at day thirty. This study substantiates prior reports that CBD and other cannabinoids are nontoxic and without fatal overdose levels.

In the present study, eight of ten participants maintained normal bilirubin levels; whereas one subject had their bilirubin return to normative values over the thirty-day period. This result stands in contrast to a recent study that found hepatoxicity of CBD in a mouse model. The present findings are also in line with other research suggesting that CBD may protect the liver from alcohol-induced damage and ischemia reperfusion injury.

Liposomal CBD, derived from industrial hemp, was provided as CELLg8™. Each 1 mL contained 10 mg of CBD from full-spectrum hemp extract, lipids derived from non-GMO sunflowers, tetrahydrocannabinol <0.05%, water <1 microS/cm, with natural plant extracts used a taste mask to mask the hemp flavor.

TABLE 1

Comprehensive Metabolic Panel Measures.

| Participant | Test | Baseline value | Day 30 value | Normal range | Change from baseline |
|---|---|---|---|---|---|
| 2 | BUN | 28 mg/dL | 28 mg/dL | 7-25 mg/dL | H to H |
| 3 | Glucose | 100 mg/dL | 88 mg/dL | 65-99 mg/dL | H to N |
| 3 | ALT | 30 U/L | 20 U/L | 6-29 U/L | H to N |
| 4 | Glucose | 103 mg/dL | 87 mg/dL | 65-99 mg/dL | H to N |
| 4 | $CO_2$ | 30 mmol/L | 31 mmol/L | 18-30 mmol/L | N to H |
| 5 | Glucose | 106 mg/dL | 94 mg/dL | 65-99 mg/dL | H to N |
| 7 | Glucose | 109 mg/dL | 91 mg/dL | 65-99 mg/dL | H to N |
| 8 | Glucose | 141 mg/dL | 99 mg/dL | 65-99 mg/dL | H to N |
| 10 | Creatinine | 1.12 mg/dL | 1.17 mg/dL | 0.5-99 mg/dL | H to H |
| 10 | Bilirubin | 1.3 mg/dL | 1.2 mg/dL | 0.5-1.2 mg/dL | H to N |

TABLE 2

Complete Blood Cell Count Measures

| Participant | Test | Baseline value | Day 30 value | Normal range | Change from baseline |
|---|---|---|---|---|---|
| 1 | RBC count | 3.95 million/μL | 4.28 million/μL | 3.96-5.31 million/μL | L to N |
| 2 | Hematocrit | 39% | 45.6% | 41.5%-53.8% | L to N |
| 2 | Absolute EOC or absolute neutrophils | 319 cells/μL | 573 cells/μL | 15-500 cells/μL | N to H |

TABLE 2-continued

Complete Blood Cell Count Measures

| Participant | Test | Baseline value | Day 30 value | Normal range | Change from baseline |
|---|---|---|---|---|---|
| 4 | Hb | 18.5 g/dL | 18.4 g/dL | 13.7-17.7 g/dL | H to H |
| 4 | MPV | 13.2 f/L | 13.5 f/L | 7.5-12.5 f/L | H to H |
| 6 | Hb | 11.7 g/dL | 11.6 g/d | 13.7-17.7 g/dL | L to L |
| 6 | Hematocrit | 36% | 35.9% | 41.5%-53.8% | L to L |
| 6 | MCH | 26.52 pg | 26.6 pg | 27-33 pg | L to L |
| 6 | RDW | 15.6% | 15.9% | 11%-15% | H to H |
| 9 | Absolute lymphocytes | 617 cells/μL | 536 cells/μL | 850-3900 cells/μL | L to L |
| 9 | Absolute EOC | 9 cells/μL | 8 cells/μL | 15-500 cells/μL | L to L |

EOC, eosinophil count; H, high; Hb, hemoglobin; L, low; MCH, mean corpuscular hemoglobin; MPV, mean plasma volume; N, normal; RBC, red blood cell; RDW, red cell distribution width.

As can be easily understood from the foregoing, the basic concepts of the present invention may be embodied in a variety of ways. The invention involves numerous and varied embodiments of a methods for treating a disorder or alleviating symptom of a disorder by orally administrating an amount of CBD over a period of time including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) methods disclosed and described, ii) similar, equivalent, and even implicit variations of each of these methods, iii) those alternative embodiments which accomplish each of the functions shown, disclosed, or described, iv) those alternative designs and methods which accomplish each of the functions shown as are implicit to accomplish that which is disclosed and described, v) each feature, component, and step shown as separate and independent inventions, vi) the applications enhanced by the various systems or components disclosed, vii) the resulting products produced by such systems or components, viii) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

What is claimed is:

1. A method of reducing fasting blood glucose level in a human subject, comprising
 orally administering daily to said human subject in need thereof an effective amount of a composition comprising: 2 mg to 15 mg of cannabidiol liposome having a concentration of cannabidiol 10 mg/mL, <0.5% tetrahydrocannabinol, and <1 microS/cm water;
 wherein said human subject has a fasting blood glucose level of 100 mg/dL to 141 mg/dL; and
 wherein said administering reduces said fasting bloodstream concentration of glucose of said human subject toward or to normative values.

2. The method of claim 1, wherein orally administering to said human about 10 mg of cannabidiol liposome once daily.

3. The method of claim 1, wherein said amount of liposomal cannabidiol is selected from the group consisting of: about 3 milligrams to about 5 milligrams, about 4 milligrams to about 6 milligrams, about 5 milligrams to about 7 milligrams, about 6 milligrams to about 8 milligrams, about 7 milligrams to about 9 milligrams, about 8 milligrams to about 10 milligrams, about 9 milligrams to about 11 milligrams, about 10 milligrams to about 12 milligrams, about 11 milligrams to about 13 milligrams, about 12 milligrams to about 14 milligrams.

4. The method of claim 1, wherein said cannabidiol obtained comprises a cannabidiol extract of a plant biomass.

5. The method of claim 4, wherein said plant biomass is hemp.

6. The method of claim 4, wherein said cannabidiol liposome comprises lipids admixed with said cannabidiol.

7. The method of claim 6, wherein said lipids are extracted from sunflower seeds.

8. The method of claim 1, further comprising a taste mask.

* * * * *